(12) United States Patent
Gramann et al.

(10) Patent No.: US 9,452,033 B2
(45) Date of Patent: Sep. 27, 2016

(54) DEVICE FOR DISPENSING A DENTAL MATERIAL

(71) Applicant: 3M INNOVATIVE PROPERTIES COMPANY, St. Paul, MN (US)

(72) Inventors: Jens Gramann, Gräfelfing (DE); Emir Jelovac, München (DE); Andreas Bergsträßer, Albaching (DE)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 0 days.

(21) Appl. No.: 14/424,330

(22) PCT Filed: Aug. 22, 2013

(86) PCT No.: PCT/US2013/056159
§ 371 (c)(1),
(2) Date: Feb. 26, 2015

(87) PCT Pub. No.: WO2014/035790
PCT Pub. Date: Mar. 6, 2014

(65) Prior Publication Data
US 2015/0216634 A1 Aug. 6, 2015

(30) Foreign Application Priority Data
Aug. 28, 2012 (EP) .................................... 12182079

(51) Int. Cl.
*A61C 9/00* (2006.01)
*B05C 17/01* (2006.01)

(52) U.S. Cl.
CPC ............ *A61C 9/0026* (2013.01); *B05C 17/01* (2013.01)

(58) Field of Classification Search
USPC .......... 222/164, 325–327, 386, 181.1, 181.2, 222/185.1; 433/49
See application file for complete search history.

(56) References Cited

U.S. PATENT DOCUMENTS

| | | | |
|---|---|---|---|
| 6,315,164 B1* | 11/2001 | Muhlbauer | A61O 5/064 222/325 |
| 2009/0279382 A1* | 11/2009 | Harre | A61C 5/064 366/133 |
| 2010/0091607 A1* | 4/2010 | Meyer | A61O 5/064 366/151.2 |
| 2010/0128559 A1* | 5/2010 | Keller | A61O 5/064 366/196 |

(Continued)

FOREIGN PATENT DOCUMENTS

| DE | 102010013750 | 7/2011 |
|---|---|---|
| EP | 1700639 | 9/2006 |

(Continued)

OTHER PUBLICATIONS

International Search report for PCT International Application No. PCT/US2013/056159 mailed on Nov. 7, 2013, 3 pages.

*Primary Examiner* — Donnell Long

(57) ABSTRACT

The present invention relates to a device (10) for dispensing a dental material. The device (10) comprises a body (12) having at least one compartment (14) for receiving the dental material, at least one piston for extruding the dental material from the compartment (14) and a drive for moving the piston and the compartment (14) relative to one another. The device (10) further comprises a stand (36) which is mounted to the body (12) such that the body (12) and the stand (36) are pivotally moveable relative to one other.

14 Claims, 4 Drawing Sheets

(56) References Cited

U.S. PATENT DOCUMENTS

2011/0259916 A1* 10/2011 Spivey, Sr. .......... B65D 5/4208
  222/105
2013/0181012 A1   7/2013 Nehren

FOREIGN PATENT DOCUMENTS

EP    1736113      12/2006
JP    04-152943    5/1992

* cited by examiner

DEVICE FOR DISPENSING A DENTAL MATERIAL

FIELD OF THE INVENTION

The present invention relates to a device for dispensing a dental material such as a multiple-component impression material used for making dental impressions of teeth.

BACKGROUND ART

In dentistry a variety of devices are available which allow for preparation and/or application of dental materials in a dentist's practice. In particular for preparation of materials that are typically used at larger amounts, like for example dental impression materials, devices have been developed that provide for automatic dispensing from packages and/or for mixing of such materials. An exemplary device for mixing and dispensing a dental impression material is for example available under the designation 3M™ ESPE™ Pentamix™ from 3M Deutschland GmbH, Germany. Typically such a device allows for two material components to be simultaneously supplied from a package through a mixer where they are mixed. Often the devices provide for continuously extruding the components through a mixer, where the components are mixed as the components flow through the mixer and released from an outlet.

The devices further typically have a motor driven piston for extruding the material from a container. A variety of different drive concepts have been proposed for driving the piston at a relatively high force as it may be required for appropriately dispensing the dental material.

For example EP 1 700 639 discloses a device for dispensing a flowable substance. The device comprises at least one force transmitting member (for example a push-pull chain) adapted to transmit a pushing force in a direction toward or opposite the substance and which can be gathered non-linearly.

Further, dispensing devices are known which are mounted to a wall above a table or another working surface at which the dispensed materials are handled.

Despite the advantages provided by the above-identified dispensing devices, there is still a potential for improvements thereof. Particularly, there is still a desire to improve the size, and particularly the footprint, and transportability of such dispensing devices.

SUMMARY OF THE INVENTION

The invention relates to a device for dispensing a dental material. The device comprises a body having at least one compartment for receiving the dental material, at least one piston for extruding the dental material from the compartment and a drive for moving the piston and the compartment relative to one another. The device further comprises a stand which is mounted or suspended to the body such that the body and the stand are pivotally moveable relative to one other.

The invention may be advantageous in that it allows an improved handling of the device concerning installation and storage. Particularly, the device may be set up for operating and may be removed for storing the device in a simple manner by pivotally moving the stand and the body relative to one another. The invention is further advantageous in that it preferably enables single handed transportation in a situation in the stand and the body are positioned for storing the device.

The body and the stand may be pivotally moveable relative to other between at least a working position, wherein the device is operable to dispense the dental material, and a storage position, wherein the device is storable. This arrangement allows a simple operation for activating and inactivating the device by means of a folding operation (toward the storage position) and an unfolding operation (toward the working position), respectively.

The device may be disposable on a working surface, wherein the body defines a longitudinal axis and the longitudinal axis intersects the working surface in the working position at an acute angle. For example, the working surface may be a generally planar surface, for example a table surface in a dentist's office or laboratory, on which the device can be disposed. Such a table usually does not provide a large area, for example for placing a device for dispensing dental material on it. As the body is inclined with respect to the working surface, the device preferably has a minimized footprint in the working position but still preferably allows the dental material to be dispensed from it.

The longitudinal axis is preferably parallel to a dimension or direction in which the piston is movable for dispensing material from the device. For example, the acute angle may be within a range of about 30° to about 45°. This range for the angle provides a good compromise between the size of the footprint and the operability of the device. Further such a position of the stand and the body relative to each other allows a user of the device to handle the dental material discharged from the device in a space between the body and the working surface.

The stand and the body may define a rotation axis which is substantially parallel to a width of the body. The body and the stand thus may be pivotally moveable relative to one other about the rotation axis. In other words, the stand and the body are preferably mounted or arranged for a pivotal movement relative to one other about the rotation axis wherein the rotation axis is arranged generally perpendicular to the longitudinal axis. This arrangement allows a simple operation for activating and inactivating the device by means of a rotational movement. The rotation axis may extend within a plane intersecting the body substantially in the middle. This arrangement facilitates a secure disposition of the device because a supporting surface for the device is located at the middle of the body. The rotation axis may for example extend within a center of gravity of the body.

For the purpose of this specification the width of the body preferably refers to a first dimension of the device which is perpendicular to a second dimension of the device, with the first and second dimension being arranged in a common plane which is arranged generally parallel to the working surface the device is disposable on. A height of the device further preferably refers to a third dimension of the device which is arranged perpendicular to the first and second dimension of the device. In the storage position at least one dimension of the device is smaller than the same dimension in the working position. For example the height or third dimension of the device may be smaller in the storage position than the height or third dimension in the working position.

In the working position the stand may be substantially perpendicular to the body, whereas in the storage position the stand may be substantially parallel to the body. In the storage position the device is preferably generally flat and thus may be conveniently transportable and/or storable, whereas in the working position the device is preferably conveniently usable with the body being securely supported by the stand.

The stand may be a flap. This arrangement allows a relatively compact assembly of the body and the stand.

The flap may be corrugated. A corrugation improves rigidity of the flap such that the flap is prevented from buckling.

The device may further comprise a handle at the body. A handle at the body improves the handling of the device as it allows a user to carry the device, for example in the storage position, or to move the device along a working surface by pulling or pushing the handle, for example in the working position). The handle is preferably arranged at the body such that the handle is operable for pivoting the body and the stand between the working and the storage position as well as such that the handle is operable for carrying the device at the handle at least in the storage position. Accordingly the handle preferably has a double function providing for two different operations.

The body may comprise an outlet for the dental material from the compartment formed in a surface of the body, wherein the handle is arranged at the body adjacent the surface of the outlet. This arrangement allows for bringing the device into an upright position by simply lifting the body at the handle.

The device may comprise a locking mechanism adapted to fix the body and the stand in one or more predetermined fixed positions relative to one another. This arrangement may prevent an undesired movement of the stand or the body relative to one another, and may allow for the device to be user adjusted in one of the predetermined fixed positions.

The stand may be mounted to the body at opposing sides of the body. This arrangement allows a support of the body, for example by means of a bearing, and a may provide a stable stand due to the suspension of the body at two points.

The stand may be "U"-shaped and adjacent ends of the legs of the U may be mounted to the body. This arrangement allows a rotational movement of the body through the legs of the stand, wherein the body is securely supported at two points. Particularly, the stand may serve as a single foot for carrying and supporting the body in a secure manner.

In the storage position, the stand may cover three sides of the body at least partially. This arrangement provides a very small footprint for the device.

It is to be noted that the stand may be directly or indirectly mounted to the body. For example, the stand may be connected to a gearbox for driving the piston or any other component of the device included or enclosed by the body. For example, the body may include a housing enclosing the drive, the compartment, the piston and the like. Alternatively, the body may be formed as a housing enclosing the drive, the compartment, the piston and the like.

Accordingly, the skilled person will recognize that the expression "mounted", which is used regarding the stand and the body, for the purpose of this specification is to be understood generally as any suitable pivotal or rotational connection of the stand and the body and in that the provision of such a connection does not necessarily include a step of mounting the stand to the body. Thus, the stand and the body may be formed as separate constructional members, which are connected to each other, or may be integrally formed. In the latter case, the stand and the body may be pivotally or rotatably connected to each other by means of a hinge such as an integral hinge.

According to a preferred embodiment, the drive for moving the piston may be a spindle drive which is operable for moving the piston. Such an arrangement may be advantageous in that it allows a relatively simple and compact design of the device. In particular complex gear boxes may not be required. A design which is enabled by the invention may further help maximizing the use of standardized components as they may be available in the industry. Such a spindle drive may further be advantageous in that it may enable relatively slow or extremely slow extrusion speeds of the dental material. This may allow the dispensation of relatively high viscous materials for example.

The device may be adapted to receive the dental material in the form of two material components. Such a device further preferably comprises at least one cartridge which contains the components of the dental material. The cartridge may have two individual compartments for containing the individual components of the dental material. The cartridge may for example be adapted for receiving a foil bag in each compartment, and each foil bag may contain a component of the dental material. A cartridge of another example may be adapted to directly contain a component in each compartment, and may comprise a plug for closing each compartment. Each plug may be adapted such that it seals with an inner wall of the compartment and such that it is movable in the compartment for extruding the component from the compartment. The device may have two pistons each being adapted to be moved into one of the compartments of the cartridge. The pistons may for example be adapted such that they can be moved into the compartments for compressing the foil bags and/or for advancing the plugs. Thus the pistons may cause the components to be extruded from the cartridge.

The device may have at least one spindle drive for driving the two pistons, or two spindle drives each driving one piston. A spindle drive for each piston may allow a relative synchronous extrusion of the components because the spindle drives and the pistons may be arranged generally coaxially with one another and aligned with the direction of force used for extruding the components. Thus tilting of the pistons relative to each other may be prevented.

The device may further comprise a mixer for mixing the components. Further the device may have a mixer shaft for receiving and driving the mixer. The mixer shaft may for example have a coupling for engaging with a coupling of the mixer. Therefore the mixer may be removably engaged with the mixer shaft. The mixer further may have two inlets each being adapted for connecting with an outlet of the cartridge. The outlets may be provided by the cartridge itself or at a part which is separable from the cartridge. For example the foil bags may comprise caps connected thereto. The caps may be receivable at and end of the cartridge and may provide an outlet for the foil bags. Further, the compartments may be closed by such caps at one end and by the plugs at the opposite end.

In the storage position and with the device standing with the stand appropriately on a horizontal surface the device is preferably oriented such that the outlets face away from that horizontal surface, particularly preferably vertically upwards. In other words in the storage position the device is preferably oriented such that the outlets of a cartridge (appropriately) inserted in the device face away from the stand. Thus the operability of the device for dispensing materials is preferably disabled in the storage position. This is because in such a storage position dispensation of dental material, for example into a dental tray is not possible. Further afterflow of any dental material (and undesired dripping onto the stand or surface) after dispensation may be avoided.

The device may comprise a spindle. The device may further comprise a link, such as a nut or clasp nut. The link is preferably engaged with the spindle. The spindle may be arranged stationary, for example stationary to the dispensing device, but rotatable thereto. The link may be connected with a piston of the dispensing device. Thus, a rotation of the link and the spindle relative to one another preferably causes the link and the spindle to displace in a direction along the spindle. This displacement may be used to move the piston via the link for extruding the dental material.

The spindle may be drivable by a motor of the device. In particular the spindle may be connected to a motor. For example, the spindle may be directly connected to a motor shaft of a motor, or the spindle may be connected to the motor via a transmission, for example a geared transmission, a belt transmission, or any other suitable transmission. The motor is preferably an electric motor, for example a DC or AC motor.

It is to be noted that any drive known to a person skilled in the art may be used for moving the pistons in order to extrude the dental material. Further, the present invention is not limited to dispensing dental material. Any suitable material may be dispensed although dental materials are preferred.

DETAILED DESCRIPTION OF THE INVENTION

Figure 1:
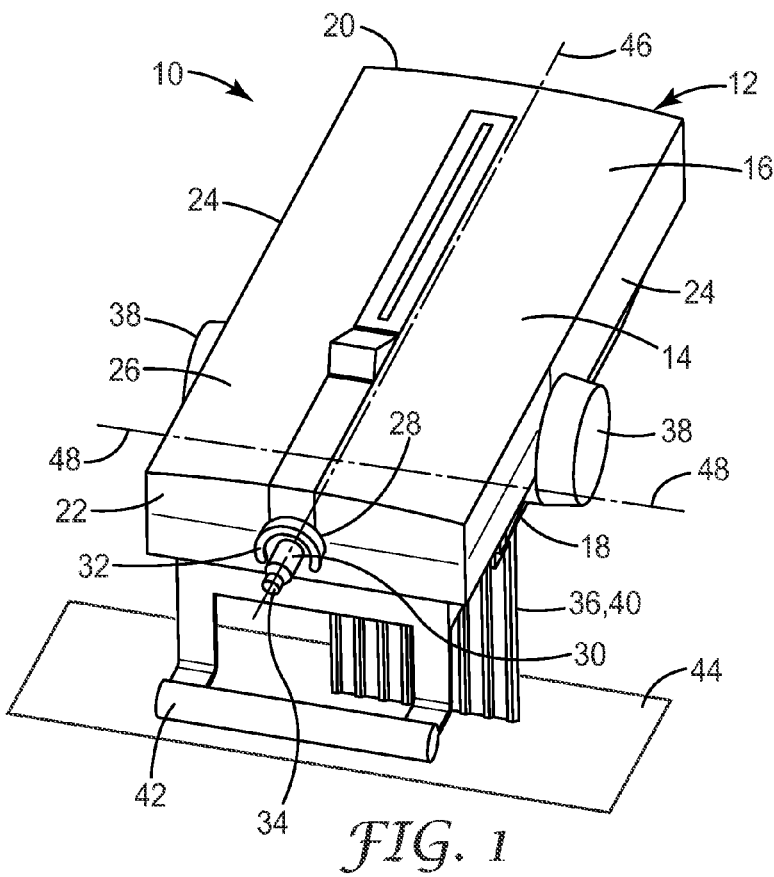
FIG. 1 is a perspective view of a device for dispensing dental material according to a first embodiment of the invention.

FIG. 1 shows a perspective view of a device 10 for dispensing a dental material according to a first embodiment. Particularly, the device 10 may be embodied as a device for mixing and dispensing dental materials. The device 10 is motorized and therefore allows for automatic dispensation of the materials. The device 10 comprises a body 12 which holds two components of a dental material in containers which are located within a compartment 14 enclosed by the body 12. The body 12 may be formed as a cuboid housing such that the body 12 comprises a front side 16, a rear side 18, a top side 20, a bottom side 22 and two side surfaces 24. The body 12 may comprise a length in a range of 300 mm to 400 mm, such as 350 mm, wherein the length of the body is a dimension parallel to the front and rear sides 16, 18 and parallel to the side surfaces 24. Further, the body may comprise a width in a range of 250 mm to 350 mm, such as 310 mm, wherein the width is a dimension parallel to the top and bottom sides 20, 22 and perpendicular to the side surfaces 24. Still further, the body 12 may comprise a height in a range of 200 mm to 250 mm, such as 235 mm, wherein the height is a dimension parallel to the side surfaces 24 and perpendicular to the front and rear sides 16, 18.

Particularly, the compartment 14 may be closed by a lid 26 provided at the front side 16. The lid 26 may be selectively opened in order to allow an insertion into and a replacement of the containers from the compartment 14. An outlet 28 for the dental material from the compartment 14 is formed in a surface of the body 12. In the embodiment shown in FIG. 1, the surface is the bottom side 22. A mixer 30 for mixing the two components of the dental material is attached to the body 12 at the bottom side 22 of the body 12. Particularly, the mixer 30 is connected to or received within the outlet 28 so as to be in communication with the containers. The mixer 30 has a mixing chamber formed between a rotatable mixing rotor and a mixer body 32. The mixer 30 is connected to the containers such that the individual components can flow into the mixing chamber. The mixture can exit through an outlet 34 of the mixer 30. The device 10 is adapted to drive the mixing rotor so as to mix the components in the mixing chamber. The device 10 may implement a continuous dynamic mixing process in which components can be continuously supplied into the mixing chamber and in which the mixture from the components can be dispensed continuously from the mixer. Thus the device 10 allows preparation for variable amounts of dental materials without the need of pre-determining amounts of initial components of the mixture. The components can be advanced toward the mixer 30 by a piston (not shown) of the device 10. Both the mixer and the piston can be driven by a not shown drive, which may be a motor connected to a spindle drive, or individual motors provided within the body 12 of the device 10.

For example, the device 10 shown in FIG. 1 may be used to mix and dispense a hardenable dental impression material. The mixed material may be used to fill a dental tray which is then placed into a patient's mouth to take a dental impression. The mixer 30 may be attached replaceably to the device 10. Therefore, when the mixed material hardens and thus blocks the mixer 30, the used mixer 30 may be replaced by an unused mixer 30 for the next use of the device 10.

Figure 2:
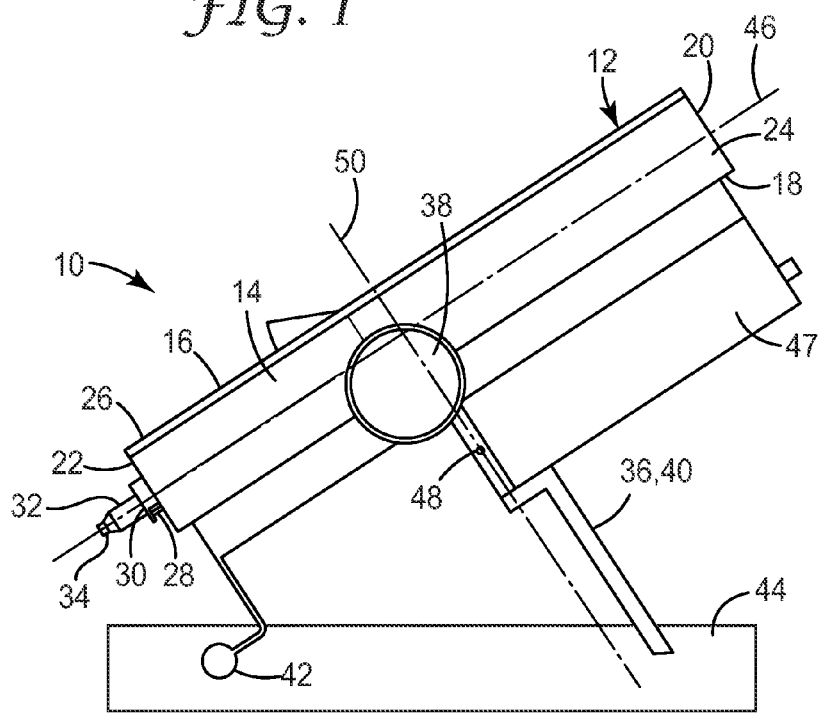
FIG. 2 is a side view of the dispensing device showing the stand in the working position.

The body 12 may enclose a spindle drive which has at least one spindle and a link (for example a nut or a clasp nut). The spindle drive may be generally used to convert a rotational input motion in a linear output motion. The linear output motion may be used to move the piston for extruding dental material from the dental dispensing device. The spindle may have a thread which is in engagement with a thread of the link. The spindle may be arranged stationary but rotatable, for example stationary relative to the dispensing device but rotatable relative thereto. Further the link may be arranged movable along the spindle but rotationally locked relative to the device. The link may be connected with one or both pistons of the dispensing device. Therefore, the spindle drive is adapted such that a rotation of the spindle and the link relative to one another causes a linear displacement of the link and the spindle relative to one another in the longitudinal dimension of the body. Further, the device 10 comprises a stand 36. The stand 36 is mounted to the body 12 such that the body 12 and the stand 36 are pivotally moveable relative to one another. For example, the stand 36 is pivotally mounted to the rear side 18. Particularly, the stand 22 may be close to knobs 38 for manually driving the piston within the body 12, wherein the knobs 38 are mounted approximately in the middle of the body 12 at the side surfaces 24 of the body 12. The stand 36 may be a flap 40. The flap 40 may be is formed in an angled manner as shown in FIG. 2. It is to be noted that the flap 40 may comprise any shape suitable to provide a support for the body 12 such as a linearly extending flap. Further, the flap 40 may be corrugated. Still further, the device comprises a handle 42 at the body 12. The handle 42 is arranged at the body 12 adjacent the outlet 28. In the embodiment shown, the handle 42 is mounted to the rear side 18 close to the outlet 28.

FIG. 2 shows the device 10 in a working position. In the working position, the body 12 is inclined in an acute angle relative to a working surface 44. The acute angle may be in a range of for example 30° to 45°, such as 40°, with respect to the working surface 44, where the device 10 is provided. The angle may be defined between a longitudinal axis 46 of the body 12 and the working surface 44 (which usually extends horizontally). In the working position the stand 36 is generally perpendicular to the rear side 18 of the body 12. The stand 36 may be fixed relative to the body 12 in the working position for example by a clamping device or any other suitable locking mechanism adapted to prevent an undesired pivotal movement of the stand 36 and the body 12 relative to one another. In the working position, the stand 36 may abut a stopper 47, which prevents the stand 36 from rotating more than the perpendicular orientation with respect to the rear side 18 of the body 12. In the working position the device 10 may stand on the working surface 44 by means of the handle 42 and the stand 36. Accordingly, the weight of the device 10 and, particularly, of the body 12 is received by the handle 42 and the stand 36. Particularly, as the handle 42 and the stand 36 are oriented substantially at a right angle relative to one another, they provide a secure support for the body 12.

Figure 3:
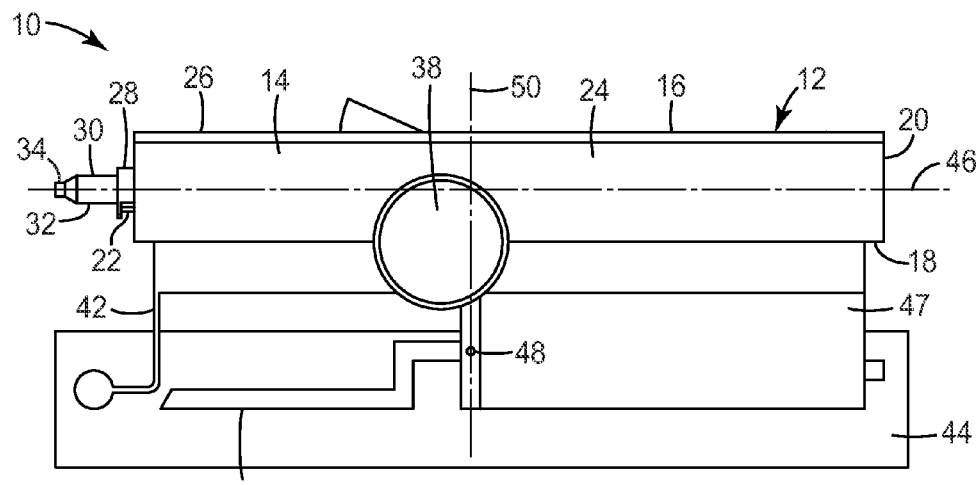
FIG. 3 is a side view of the dispensing device showing the stand in the storage position.

FIG. 3 shows the device 10 in a storage position. In the storage position, the stand 36 is almost parallel to the rear side 18 of the body 12. In the storage position, the device 10 is disposed at the working surface such that the rear side 18 contacts the working surface 44 and is parallel thereto. Particularly, in order to move the device from the working position into the storage position, the stand 36 is pivoted towards the handle 42. This means, the stand 36 and the body 12 may be pivoted relative to one another from the working position into the storage position and vice versa for moving the device 10 from the storage position into the working position. Particularly, the stand 36 and the body 12 may define a rotation axis 48, which is substantially parallel to a width of the body 12. The rotation axis 48 extends within a plane 50 intersecting the body 12 at substantially in the middle. The stand 36 and the body 12 may be rotated around the rotation axis 48 relative to one another. As shown in FIG. 3, in the storage position, the device 10 is provided in a flat state, such that for example the device 10 can be stored in a drawer.

Figure 4:
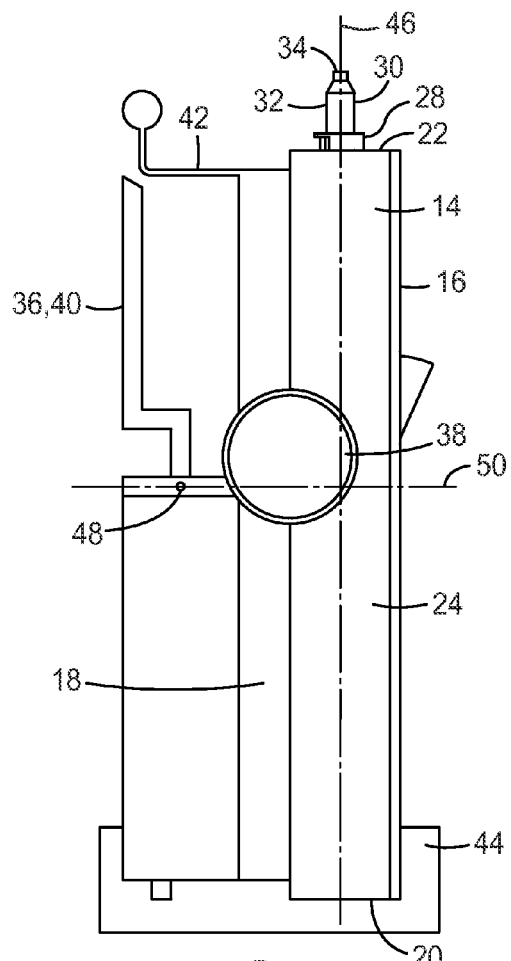
FIG. 4 is a side view of the dispensing device showing the dispensing device in the storage position.

FIG. 4 shows the device 10 in the storage position but oriented generally vertical. As illustrated the storage position allows the device 10 to be brought in an upright position for minimized footprint. Particularly, the body 12 stands on the top side 20 such that the mixer 30 is opposite to the working surface 44. In other words, in the position and orientation shown, the mixer faces away from the working surface 44. The storage position further allows the device 10 to be disposed close to or at a wall or the like and only needs a minimal footprint for storing the device.

Figure 5:
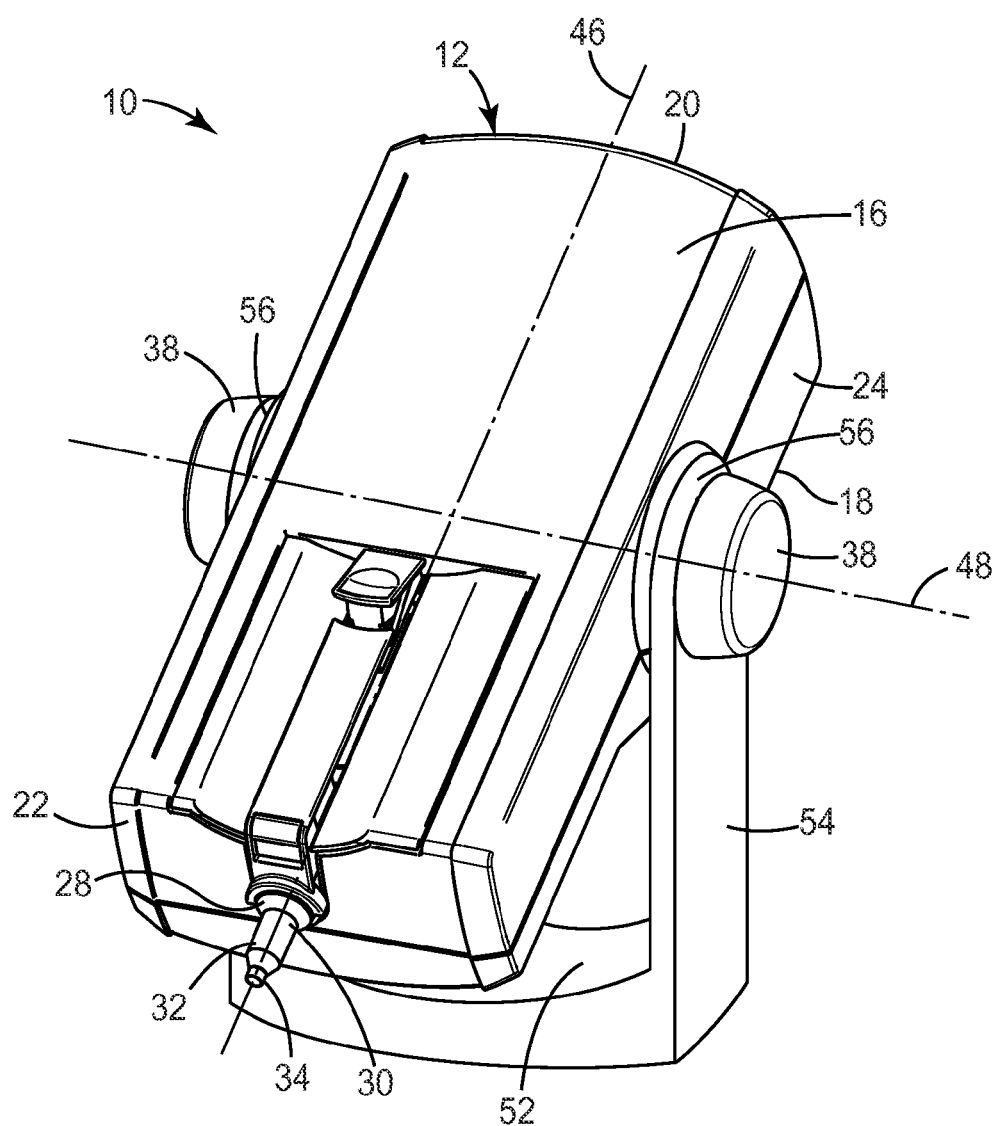
FIG. 5 is a perspective view of a device for dispensing dental material according to a second embodiment of the invention.

FIG. 5 shows a second embodiment of the device 10. It is to be noted that only the differences from the first embodiment are explained and like constructional members are denoted by like reference numerals. According to the second embodiment, the body 12 is pivotally mounted relative to the stand 36. Further, the handle 42 is omitted such that the stand 36 provides the only support for the body 12. Particularly, FIG. 5 shows the device 10 in the working position. In the working position, the body 12 is inclined with respect to the stand 36 as shown in FIG. 5. As the stand 36 is disposed on the working surface 44, the inclination may be defined between the longitudinal axis 46 and the working surface 44. Particularly, in the working position, longitudinal axis 46 intersects the working surface 44 at an acute angle in a range of 30° to 45°, such as 40°.

According to the second embodiment, the stand 36 is substantially "U" shaped. The stand 36 comprises a bottom part 52, which is adapted to be disposed on the working surface 44 or the like, and two opposing or adjacent legs 54 of the "U", which extend perpendicular to the bottom part 52. The stand 36 is mounted to the body 12 at opposing sides of the body 12. For example, the stand 36 is mounted to the body 12 at the side surfaces 24 thereof. Particularly, adjacent ends 56 of the legs 54 are mounted to the body 12. As shown in FIG. 5, one respective end 56 of the legs 54 is mounted to the body 12 between one respective knob 38 and one respective side surface 24 of the body 12. In this embodiment, the rotation axis 48, around which the relative pivotally movement of the body 12 and the stand 36 is allowed, extends through the knobs 38.

Figure 6:
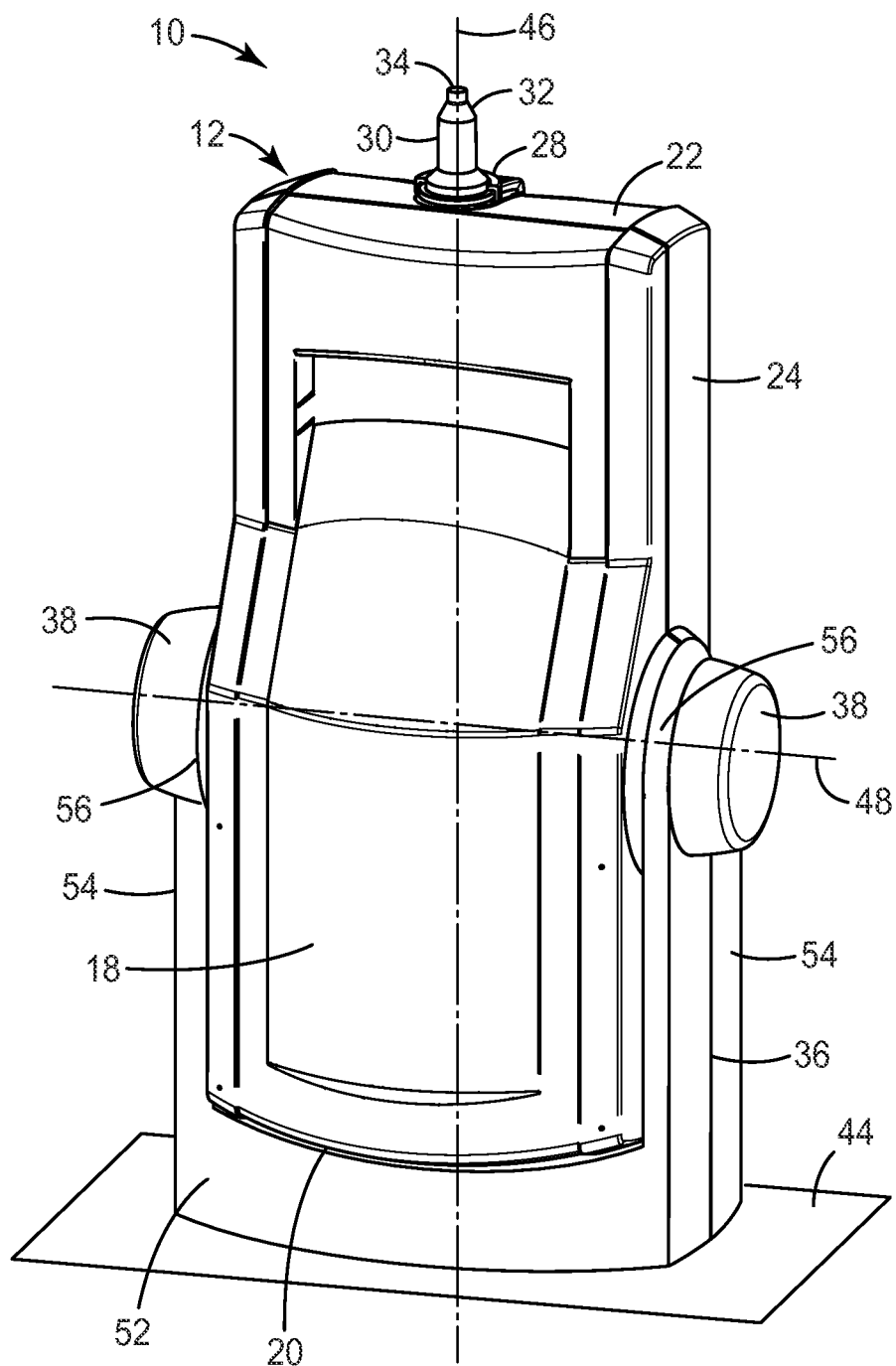
FIG. 6 is a perspective view of the dispensing device according to the second embodiment shown in the storage position.

FIG. 6 shows the device 10 in a storage position. In the storage position, the body 12 is pivoted in an upright position, in which the mixer 14 faces away from the working surface 44. As shown in FIG. 6, in the storage position according to the second embodiment, the stand 46 covers three sides of the body 12 at least partially. In this embodiment, the three sides are the bottom side 22 and the side surfaces 24.

It is to be noted that also in the second embodiment, a locking mechanism may be provided which prevents an undesired rotation of the body 12 and the stand relative to one another. Further, it is explicitly mentioned that a security device may be provided for securing that the dispensing device 10 may be activated only in the working position for dispensing the dental material in order to ensure the prevention of an undesired dispensing of the dental material. For example, such a security device may be or may include a switch or a electric circuit or the like, which allows a dispensing only in the working position.

What is claimed is:

1. A device for dispensing a dental material, comprising:
a body having at least one compartment for receiving the dental material, at least one piston for extruding the dental material from the compartment and a drive for moving the piston and the compartment relative to one another, wherein the device further comprises a stand which is mounted to the body such that the body and the stand are pivotally moveable relative to one other, wherein the body and the stand are pivotally moveable relative to one other between at least a working position, wherein the device is operable to dispense the dental material, and a storage position, wherein the device is storable, and wherein the device further comprises a handle at the body, the handle being arranged at the body such that the handle is operable for pivoting the body and the stand between the working and the storage position as well as such that the handle is operable for carrying the device at the handle at least in the storage position, wherein the body comprises an outlet for the dental material from the compartment formed in a surface of the body, and the handle is arranged at the body adjacent the surface of the outlet and extending across a portion of the body adjacent the outlet.

2. The device of claim 1, wherein the device is disposable on a working surface, wherein the body defines a longitudinal axis and the longitudinal axis intersects the working surface in the working position at an acute angle.

3. The device of claim 2, wherein the acute angle is within a range of 30° to 45°.

4. The device of claim 1, wherein the stand and the body define a rotation axis which is substantially parallel to a width of the body.

5. The device of claim 4, wherein the rotation axis extends within a plane intersecting the body at substantially in the middle.

6. The device of claim 1, wherein in the working position the stand is substantially perpendicular to the body, whereas in the storage position the stand is substantially parallel to the body.

7. The device of claim 1, wherein the stand is a flap.

8. The device of claim 7, wherein the flap is corrugated.

9. The device of claim 1, further comprising a locking mechanism adapted to fix the body and the stand in a fixed position relative to one another.

10. The device of claim 1, wherein the stand is mounted to the body at opposing sides of the body.

11. The device of claim 10, wherein the stand is "U"-shaped and adjacent ends of the legs of the "U" are mounted to the body.

12. The device of claim 11, wherein in the storage position, the stand covers three sides of the body at least partially.

13. The device of claim 1, wherein the handle extends away from the portion of the body adjacent the outlet.

14. The device of claim 13, wherein the handle is "U"-shaped.

* * * * *